(12) United States Patent
Neuberger et al.

(10) Patent No.: US 6,261,310 B1
(45) Date of Patent: Jul. 17, 2001

(54) LASER SAFE TREATMENT SYSTEM

(75) Inventors: Wolfgang Neuberger, F. T. Labuan (MY); Michael Quade, Bonn (DE); Bolesh Skutnik, West Hartford, CT (US)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/427,871

(22) Filed: Oct. 27, 1999

(51) Int. Cl.[7] ................................... A61N 5/067
(52) U.S. Cl. ................... 607/89; 606/2; 606/13; 606/16; 606/17; 600/21
(58) Field of Search .................. 606/1, 2, 9, 13, 606/16–18; 607/88–91; 128/856, 917; 600/21

(56) References Cited

U.S. PATENT DOCUMENTS 4,998,538 * 3/1991 Charowsky et al. ............. 128/856
5,728,041 * 3/1998 Fowler et al. ..................... 600/21
5,820,625 * 10/1998 Izawa et al. ........................ 606/9
5,877,825 3/1999 Kotler .

OTHER PUBLICATIONS

Data sheet for Lexan : Light Transmission vs. Wavelength, GE Polymerland, Inc., Oct. 2000.*

* cited by examiner

Primary Examiner—Linda C. M. Dvorak
Assistant Examiner—Roy Gibson
(74) Attorney, Agent, or Firm—Bolesh J. Skutnik; B J Associates

(57) ABSTRACT

In the present invention a laser treatment system is provided that can be used in any clinical environment without the necessity of personal safety equipment. Furthermore, the present invention provides a large amount of control to the operator/technician and the patient. The present invention combines mechanical and optical methods to protect operators and patients from undesired exposure to laser radiation. According to this approach, safe, portable and fixed embodiments that are useful in a large variety of applications, which are now possible. Several examples are described.

19 Claims, 8 Drawing Sheets

LASER SAFE TREATMENT SYSTEM

BACKGROUND OF THE INVENTION

1. Field of the Invention

The present invention relates to the safety measures required in the medical field to protect patients and operators from undesired radiation exposure.

2. Invention Disclosure Statement

Modern laser therapy has gained a well-accepted role in many classical parts of medical therapy methods. Nearly every procedure that employs conventional heat producing sources such as microwaves or electromagnetic field applications can also be performed using laser sources at a correct wavelength. Laser heat sources are an advantage over the prior art, because the area to be treated can be targeted specifically. The laser wavelength can be matched to the absorption wavelengths of water or hemoglobin to more accurately treat a medical problem. Suitable laser sources with sufficiently high output powers have become commercially available. Significant progress has been made in designing medical application lasers such as Q-switched Neodymium family lasers, compact carbon dioxide lasers, and in particular diode lasers.

Medical laser therapy methods are generally divided in two substantial classes: direct open treatment and interstitial treatment. In interstitial treatments, q-switched lasers are often coupled with optical fibers for use in surgery. Laser energy has also been used indirectly in treatments such as Photodynamic Therapy (PDT). In PDT, laser radiation is used to activate photo-reactive substances, which have been applied to a particular treatment zone.

There are many safety issues to be concerned with however, when using lasers in the place of conventional heat producing sources. With interstitial laser treatments such as ocular, vein treatment, hair removal, and other comparable treatments, there is less risk that the operator will be exposed to laser radiation. For many surface treatments however, many safety precautions must be taken to protect the operator and patient. State of the art systems often require cumbersome or expensive safety equipment. For example some laser systems include auto-locking doors for the operation room that cannot be opened from the outside while the laser source is running. These auto-locking doors prevent unprotected personnel from entering the treatment room. These safety requirements also mean that most laser equipment can only be used in a clinical setting. It would be advantageous if a system that fulfilled the safety requirements could be used in non-clinical settings.

U.S. Pat. No. 5,877,825 describes a type of protective eyewear for use with a pulsed laser radiation source. This protective device incorporates an electro optical shutter that causes the safety glasses' lens to become opaque during each pulse of radiation. The drawback to this invention is that every technician present must be tied into the protective system. Furthermore, this invention does not protect anyone who enters the treatment room by accident.

Many laser safety systems employ state of the art in situ visualization methods such as CCD cameras, image viewing, and processing units. This method eliminates an operator's exposure to laser radiation. Many surgeons and technicians however, prefer to operate using their own eyesight.

It is therefore the goal of the present invention to provide a method to protect medical personnel from exposure to laser radiation. The current invention will allow surgeons and technicians to use their own sight to perform operations, while still meeting safety requirements. The limitations of the prior art are overcome by the utilizing the current invention system.

BRIEF SUMMARY OF THE INVENTION

It is an object of the present invention to incorporate into a laser treatment system safety means that allow the laser system to be used more efficiently and safely.

It is another object of the present invention to provide a laser treatment system that can be used in a non-clinical setting while still meeting safety requirements.

It is also an object of the present invention to provide means by which laser treatment systems can be used more easily while still protecting the operator from laser radiation.

It is a further object of the present invention to allow the operator to visually observe the procedure without exposure to stray laser radiation.

It is yet another object of the present invention to provide a laser treatment system that protects technicians and patients from accidental exposure.

In the present invention a laser treatment system is provided that can be used in any clinical environment without the necessity of personal safety equipment. Furthermore, the present invention provides a large amount of control to the operator/technician and the patient. The present invention combines mechanical and optical methods to protect operators and patients from undesired exposure to laser radiation. According to this approach safe portable and stationary embodiments that are useful in a large variety of applications, are now possible. Several examples are described.

The above, and other objects, features and advantages of the present invention will become apparent from the following description read in conjunction with the accompanying drawings, in which like reference numbers in different drawings designate the same elements.

DETAILED DESCRIPTION OF PREFERRED EMBODIMENTS

The present invention provides an apparatus, which can be used in any clinical environment without the necessity of personal safety equipment. The present invention also gives a large amount of control to the operator as well as the patient. The present invention fulfills laser safety requirements and can be applied to emergency rescue operations or for veterinary applications as well. In these applications, the current precautions often are particularly difficult to sustain. By combining mechanical and optical methods, this approach can be applied to fixed as well as portable devices in a large range of medical applications. The present invention combines ease of use with flexibility. For example, in one embodiment a portable laser disinfecting system is used in ambulances because under the present invention it could be manufactured to meet safety requirements in such use.

Figure 1:
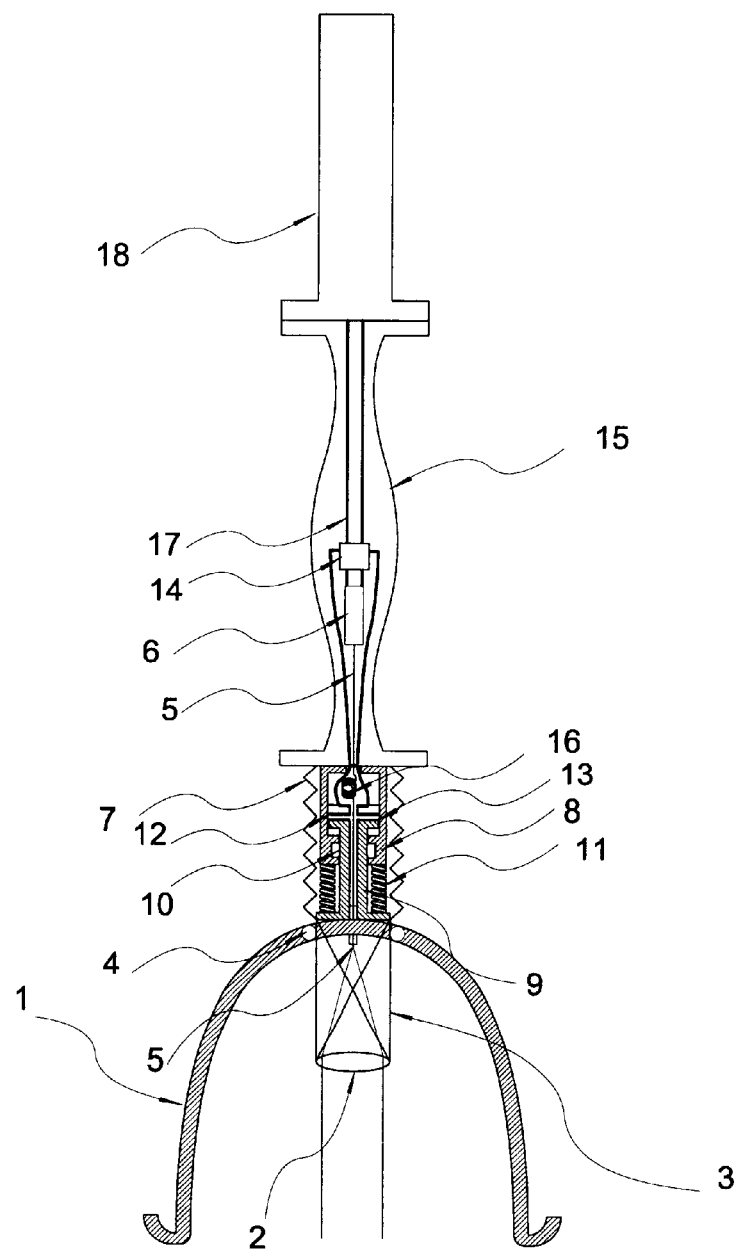
FIG. 1 depicts a conical bell shaped safety treatment system of the present invention.

FIG. 1 illustrates the basic design of a present invention embodiment. The interface towards the patient is formed by conical "bell" 1. Alternatively, the specific form of bell 1 may vary depending upon the desired treatment method and the particular optical system chosen. Furthermore, varying sizes of bell 1 are used depending on the type of treatment application area. Bell 1 is made of a transparent material, which is manufactured with a filter coating on the inside. The filter coating inside bell 1 is chosen to be highly reflective for the particular laser wavelength used. The coating should reflect all angular variation that may occur. Conversely, the coating should allow any wavelength not being used in the medical procedure to transmit and pass though. In an alternative, the bell material absorbs a sufficient amount of laser radiation to protect the operator. The bell material can be a colored glass or plastic. Since bell 1, filters out the laser radiation being used in treatment, the potential risk to patient and operator are eliminated. Bell 1 is pressed upon the body area to be treated. This means that anyone exterior to the bell is protected from the laser radiation produced in the interior. Furthermore, since the coating transmits most wavelengths other than the base wavelength, it is possible to visually inspect the treatment area during a medical procedure. Casual light will pass through the walls of the bell.

Inside the bell-shaped form of FIG. 1 are imaging optics for the radiation source. The setup presented in FIG. 1 includes lens 2, which is mounted in glass tube 3. Glass tube 3 is transparent to the radiation wavelength used in the desired application. Alternatively, glass tube 3 is antireflection coated. In yet another alternative glass tube 3 is in a stable wire frame unit. In another alternative embodiment, the lenses are exchangeable and can be mounted at different positions in the rod. This allows the radiation spot sizes to be varied. In yet another alternative, multiple lenses are used to achieve more complex irradiation profiles such as a cylindrical form or spread point images. These profiles can be achieved be using diffracting optics such as gratings. Holder 3 is passed through bell 1 and fastened to bell 1 using flexible fasteners 4. Flexible fasteners 4 allow the laser to move during treatment instead of irradiating a fixed spot. The present invention allows the intensity focused upon any part of the treatment area to be controlled. This is an advantage considering that diseased areas are rarely homogenous. At the top of the unit described in FIG. 1, at least one optical fiber 5 transports the radiation produced by an appropriate beam source 6. Beam source 6 is located elsewhere in the holder. In an alternative, multiple beam sources are used. The fiber is fixed in position to avoid altering the imaging to the treated body parts. The fiber travels completely through power control unit 7 of the invention.

Figure 1A:
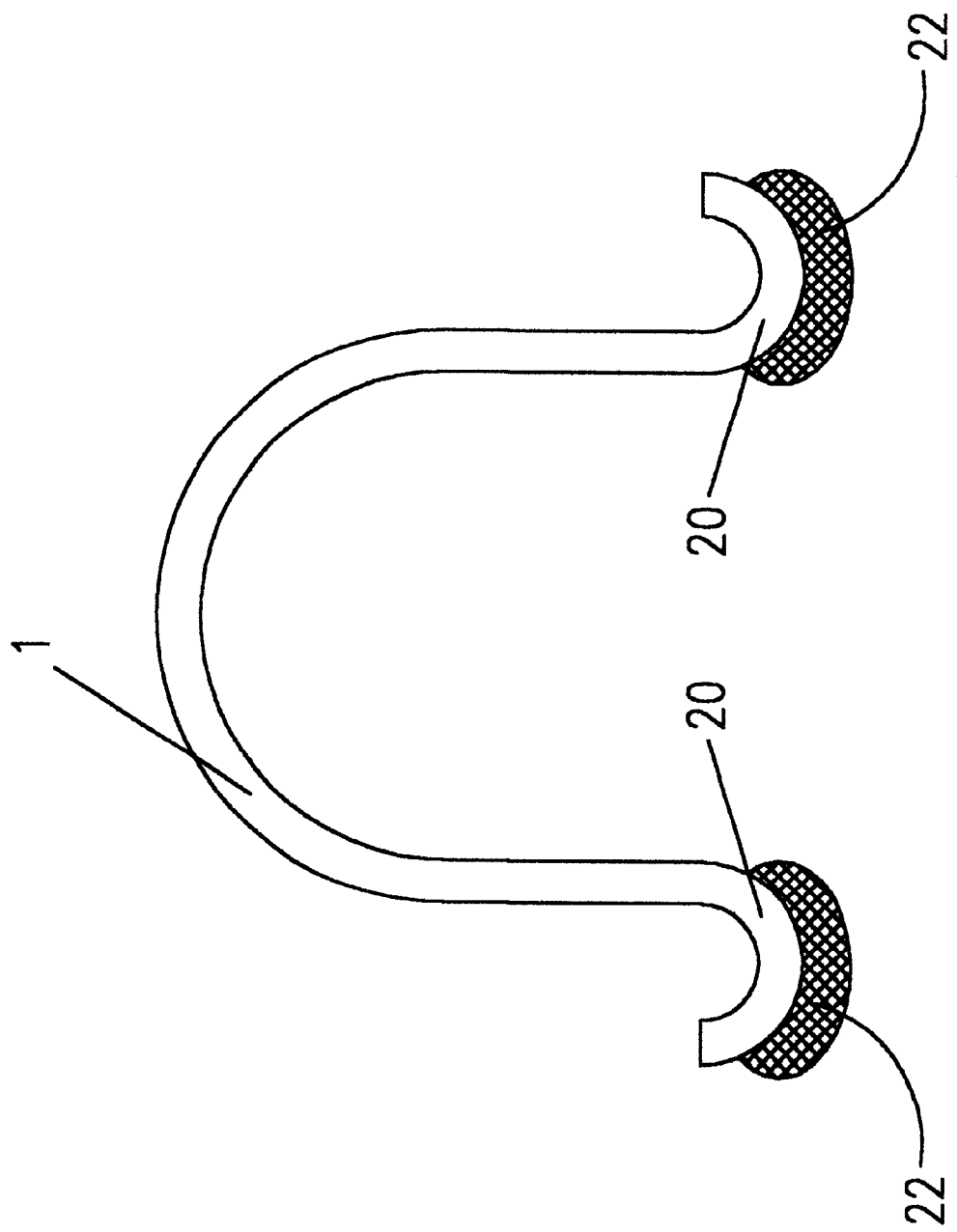
FIG. 1a shows a variation of bell 1 in FIG. 1.

FIG. 1a shows a variation of bell 1 in FIG. 1. Rim 20 of bell 1 has attached to it a soft deformable cushion 22. Cushion 22 contacts the treatment surface. This cushion makes a better easier seal between rim 20 and the surface to be treated. Therefore any leakage of laser radiation is minimized. A hard surface with an irregular pattern in the perpendicular direction would especially create a problem for sealing the treatment area. Cushion 22 provides a tighter fitting interface without causing discomfort to the patient by increasing pressure on the rim. In an alternative cushion rings of varying diameter can be manufactured to fit different sized bell/cones. In another alternative, the cushions are manufactured with a temporary adhesive. This adhesive allows the cushion to be replaced after use or interchanged with a different thickness. Alternative to using a cushion, the entire bell is manufactured from a partially flexible substance. These variations on bell 1 also benefit present invention applications that require a partial vacuum on the enclosed volume within the bell/cone. The lower vacuum would cause less discomfort to the patient and potentially less damage to non-medical substrate requiring laser treatment.

Figure 2:
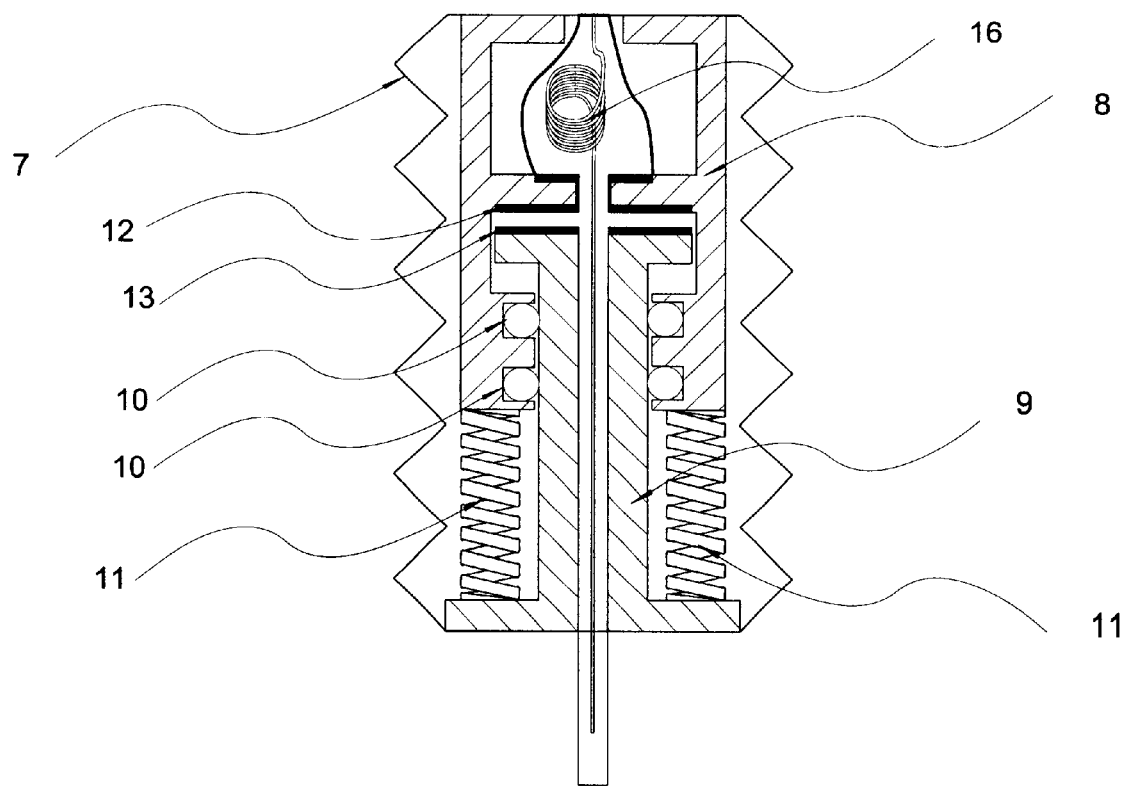
FIG. 2 illustrates the present invention power control unit in greater detail.

FIG. 2 illustrates power control unit 7 of FIG. 1 in greater detail. The power control unit is fixed to the imaging optics holder. The power control unit consists of two basic parts: upper contact shaft 8 and lower contact shaft 9. Lower contact shaft 9 is fixed to optical holder 3 shown in FIG. 1. Upper contact shaft 8 shown in FIG. 2 is movable with reduced up and down friction due to roller bearing 10. Roller bearing 10 is included in lower shaft 9. The initial position of lower shaft 9 is an elevated state due to the pressure from compression spring 11. This elevated position keeps upper contact shaft's 8 electrodes 12 separated from lower contact shaft's 9 electrodes 13. Lower shaft electrodes 13 are electrically isolated from the shaft itself. When electrically connected, all of them have the same potential. Upper shaft electrodes 12 consist of at least two separated elements at a different potential, which are therefore electrically isolated. When upper shaft 8 is pressed down against compression springs 11, upper shaft electrodes 12 will contact lower shaft electrodes 13. This closes the optical switch, which is made up of electronics 14 (shown in FIG. 1). This switch mechanism is an integral part of the present invention safety mechanism. Upper contact shaft 8 of FIG. 2 is fixed to hand-piece 15 of FIG. 1. Hand-piece 15 serves as a handle for the present invention laser tool. Bell shaped cone 1 (shown in FIG. 1) is positioned over the treatment zone. The laser operation cannot be started unless the operator presses down on hand-piece 15. This pressing creates electrical contact in power control unit 7 to start the laser operation. This assures that no radiation can enter from the exterior, because the apparatus is pressed over the treatment area, which creates a tight enclosure. The included optical fiber must be slightly longer to match the path difference that occurs due to pressing the apparatus down. Means such as loop 16 of FIG. 2 solve this problem. If necessary, multiple fiber loops are created. Power control unit 7 is completely enclosed in a suitable flexible pipe to accommodate these dimension changes made by pressing.

Beam source 6 (shown in FIG. 1) is located within the hand-piece itself. Beam source 6 is a diode laser which is fiber coupled to at least one optical fiber. Alternatively beam source 6 is a miniaturized diode pumped solid-state laser operating at a fundamental wavelength between 1 $\mu$m and 3 $\mu$m. The latter alternative can further contain means for frequency conversion that allows visible wavelengths that may have different absorption characteristics as well. In another embodiment the invention further includes means for Q-switching of this laser. In an alternative (with any chosen beam source), the beam source parameters are set externally by switches (not shown) on hand-piece 15. The parameters that are set externally include pulsed/cw operation, laser power level, duty cycle and repetition rate. Additionally switching system 14 of several relays is included. Switching system 14 is connected to power source 18. In an alternative, a state of the art battery provides power source 18. Wiring 17 connects battery power source 18 to beam sources 6 and switching unit 7. Using standard electronics, the power control unit may be operated at non-critical levels, such as 5 Volts, and current peaks can be avoided. Alternatively, the battery can be taken out of the element for recharging, while a fully charged battery replaces it to ensure continuous operation of the apparatus. In yet another embodiment, a power supply (not shown) is connected to the battery port of the apparatus to provide equivalent power from a stationary plug.

Figure 3:
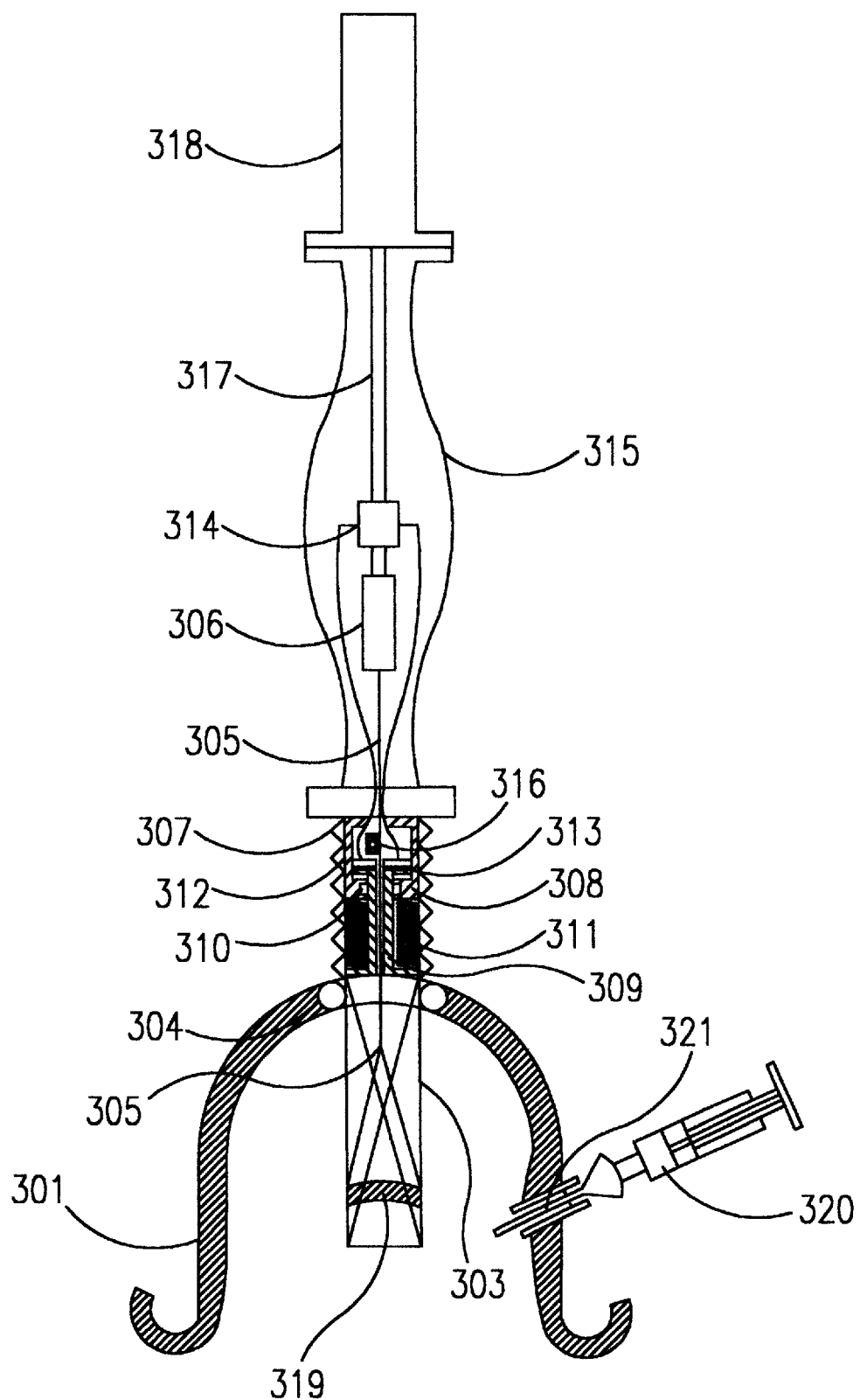
FIG. 3 depicts a present invention device with alternative imaging optics.

FIG. 3 shows a variation of the above-described concept. There are two basic variations. First, the imaging optics are completely different. Optics holder 303 is similar in design to the one in FIG. 1. Optics holder 303 holds curved mirror 319. Mirror 319 is depicted as having a defocusing effect. In an alternative, mirror 319 has a focusing effect. The radiation emitted by the fiber is reflected from mirror 319 through transparent optics holder 303 to the reflecting bell. The exact form of the bell is determined by the optical requirements. Usually the bell form is either parabolic or spherical in shape. Both alternative shapes have the effect of collimating or focussing the incoming radiation to the treatment zone. While the parabolic shape has the advantage of lower imaging errors, the spherical shape has more flexibility in uses. In an alternative, additional lenses are added to optics holder/mount 303. By varying the parameters of the lenses, the back reflecting mirror and the reflecting bell optics, the instrument can be used in a greater variety of applications/ treatments.

Second, syringe 320 is added through a lumen 321. Syringe 320 is added in a lower, non-irradiated portion of the bell. This allows the in situ addition of therapeutic substances, such as disinfectants, anaesthetic substances or PDT liquids. This allows the operator to apply therapeutic substances as needed during the operation. Furthermore, since the operator can visually inspect the treatment area, the operator can more accurately gauge the amount of therapeutic substance to apply. Alternatively, a vacuum line connects to the system through interface lumen 321. This vacuum line can be used either as part of the treatment procedure or as an additional safety mechanism. In another alternative embodiment, the pressure within the bell is monitored. Once the bell is pressed onto a treatment site, the air is partly evacuated through this vacuum line. The apparatus is designed so that the laser can only be started once a specific reduced pressure level is reached. This mechanism ensures that the bell forms an isolated treatment chamber and that no radiation can leave the chamber. Using this method, prior art safety methods such as glasses, special clothes or gloves, or constructive safety means such as emergency locks at laboratory doors all become unnecessary.

Figure 4:
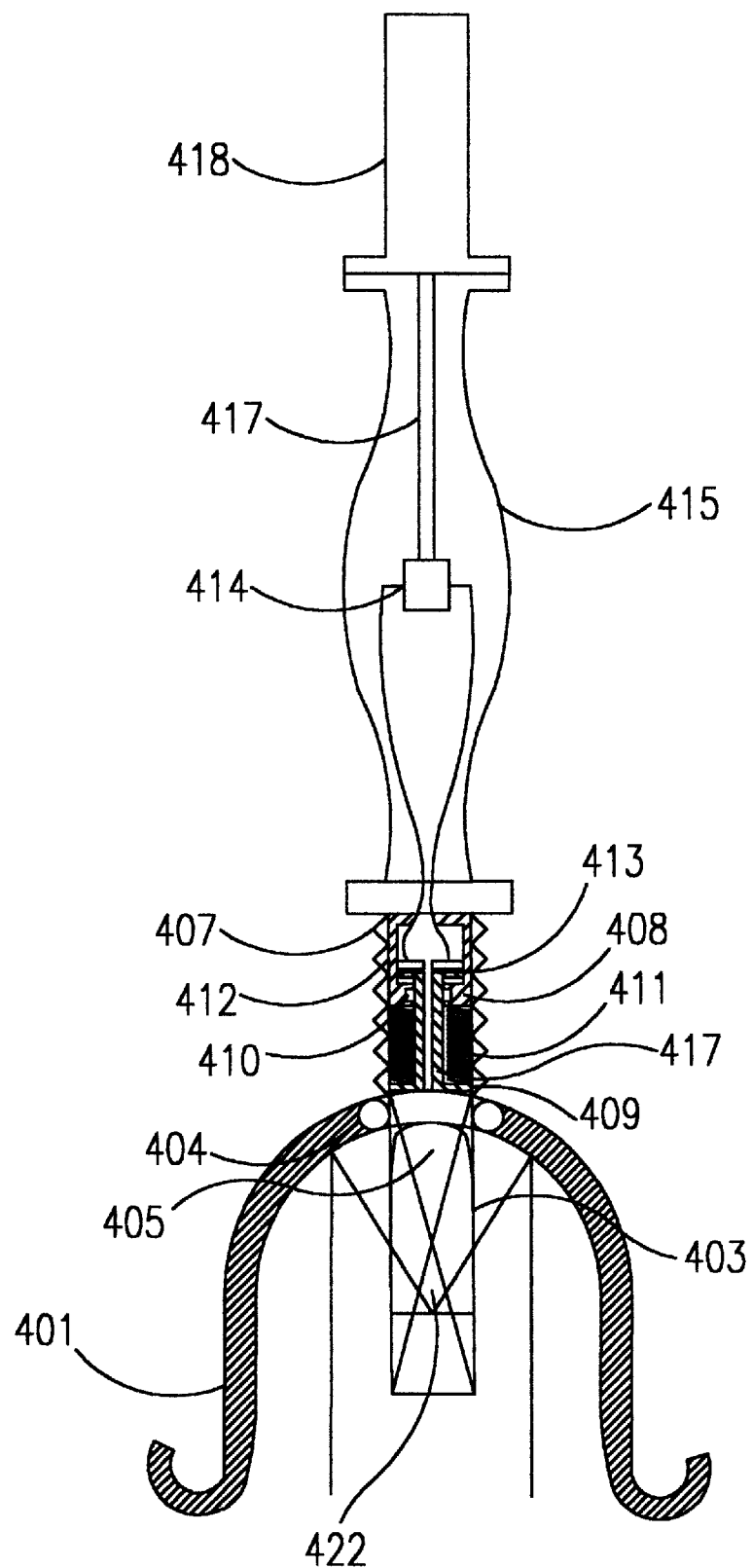
FIG. 4 shows a present invention device that incorporates an optical fiber.

FIG. 4 illustrates another basic design to the present invention. In order to reduce costs it is an advantage to directly apply the laser source instead of first coupling it to a fiber. This also enhances the electrical to optical efficiency and avoids the complications with coupling fiber to a laser source. The drawback to direct laser application in the past is that advanced constructional means were needed. In a present invention embodiment, a simple approach is taken. The beam source itself is included in optics holder 403 or 404 and images the radiation through working bell shaped cone 401 to the diseased body parts. In a preferred embodiment the laser source is placed with the aid of a transparent optics holder 403, similar to the holder described in FIG. 1.

The laser source then radiates towards the bell surface. In one embodiment micro-optical elements 405 and standard optical elements 422 shape the radiation before it hits the inner bell surface. At the inner bell surface it is directed by mirror to the treatment zone. The bell shape is manufactured to obtain ideal irradiation intensity. Preferred forms for the bell are parabolic, hyperbolic or spherical shapes. Alternatively the bell shape may be x.y astigmatic bodies that combine the above shapes with different parameters or combinations of different ones. For example, an x-parabolic can be combined with a y-spherical shape in order to correct typical diode laser astigmatisms or to equalize differences in beam quality in the two directions. Electric circuitry 417 used to drive the beam source, is guided through shaft contact system 412 and transparent holder 403 to the beam source. All other details of this apparatus are manufactured similar to the description for FIG. 1.

Figure 5:
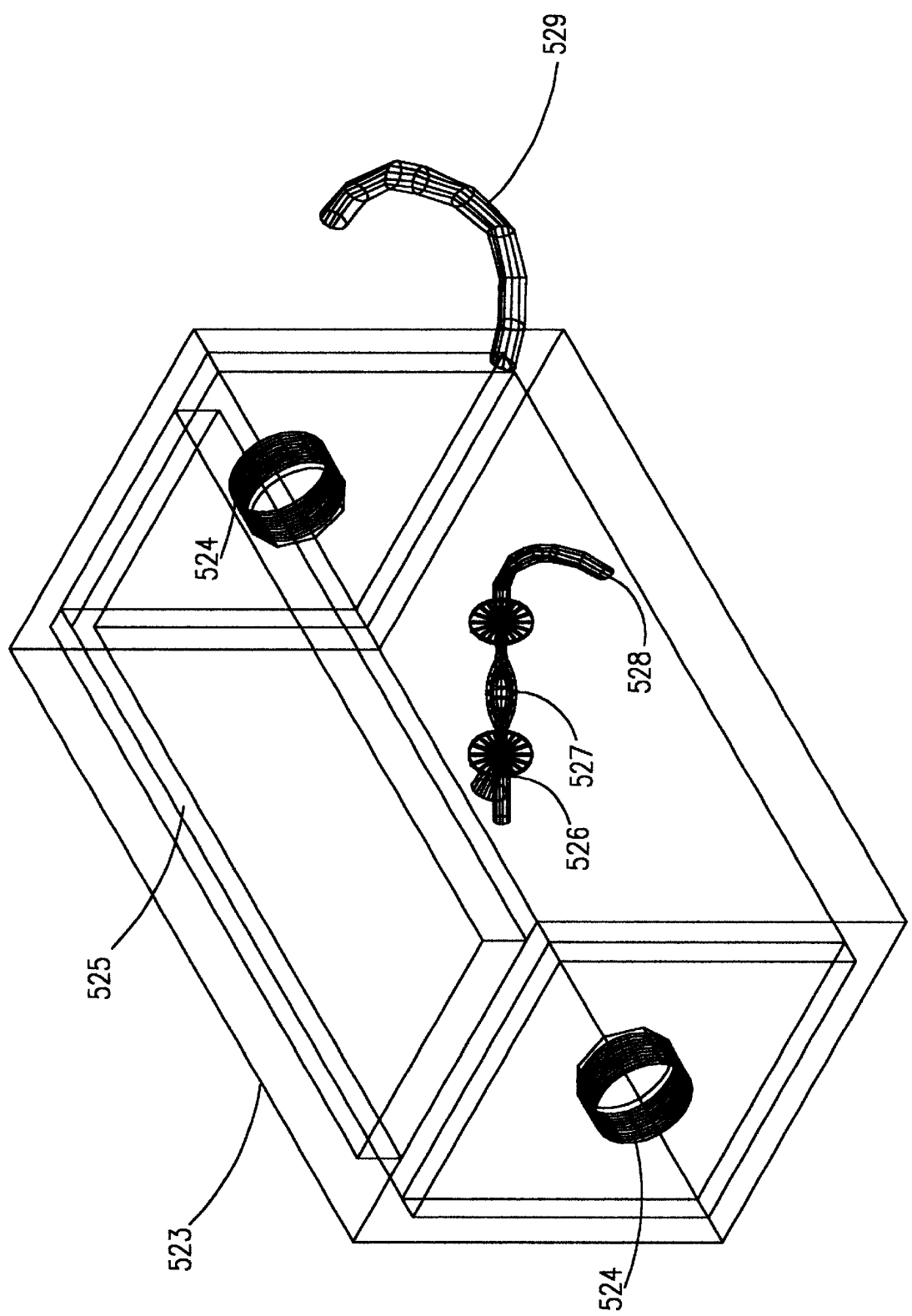
FIG. 5 illustrates a closed box embodiment of the present invention.

Another approach to resolve the problems described above concerning the laser safety during the treatment and the inspection of the treatment process, can also be solved by a stationary apparatus. This stationary apparatus satisfies the high safety demands for a system in a clinical environment. A system of this type must fulfill the highest safety standards for operator and patient, while still providing high ease of use, rapid device preparation and visual online inspection. FIG. 5 illustrates an apparatus designed to fulfill all of these requirements. This embodiment is comprised of closed box 523 made of a highly durable material. This material is chosen to be indestructible by any direct or indirect laser irradiation applied during a treatment procedure.

The part of the body to be treated is passed through holes 524. Holes 524 enclose the body part with a rubber ring, so that the interior of the box is sealed from the outside. The rubber ring is designed so that it can either withstand an evacuation to a specified low pressure or withstand an air pressure created artificially within the chamber. In alternative embodiments the pressure changes can be used to contribute to the treatment process. The pressure change however, is preferably used as a safety mechanism. A vacuum line, resp., gas or air pipe is lead through pipe 529 to the chamber. The apparatus is designed so that electrical lines for any kind of control mechanisms are guided and introduced into the chamber in a way that preserves the isolation of the interior. In a preferred embodiment, one of the control lines incorporates a pressure measurement sensor (not shown). When an exterior laser supply mechanism is used, this element is connected to the general supply (not shown). The pressure inside the chamber is detected by measurement equipment. If the pressure has reached a specified critical value, the safety mechanism allows the operator to start the laser source. For example, a specific evacuation level is used as the criterion that allows the laser system to start.

The box in this embodiment contains at least one hole enclosed with coated window 525. Coated window 525 is manufactured from any suitable glass, crystal or polymer material. The coating on window 525 is designed in a dichroitic way, so that it protects the outer environment from the application laser, while still allowing the visual inspection of the treatment area. The chromatic distortions are insignificant because typical illumination light consists of different wavelengths than most processing lasers. This is particularly true because many medical operation lasers operate in the infrared region. Even for lasers that operate in visible wavelengths, the chromatic distortions do not significantly effect affect treatment area visualization. Alternatively window 525 is manufactured from a colored material.

The colored material absorbs the active laser wavelength to protect the operator from the particular visible or non-visible wavelength being used.

The application instrument itself is introduced into the box through isolating interface 526. In this embodiment it consists basically of the same elements as the instrument in FIG. 1. The application instrument is preferably hand-piece 527 which contains power control means. The power control means can be realized by switches, pressure controls or a foot-piece. The laser unit has a flexible interface, so that it can be moved over a large distance in the chamber. The flexibility allows the laser unit to cover large treatment areas or to perform the necessary movements in applications such as vessel treatments.

Figure 6:
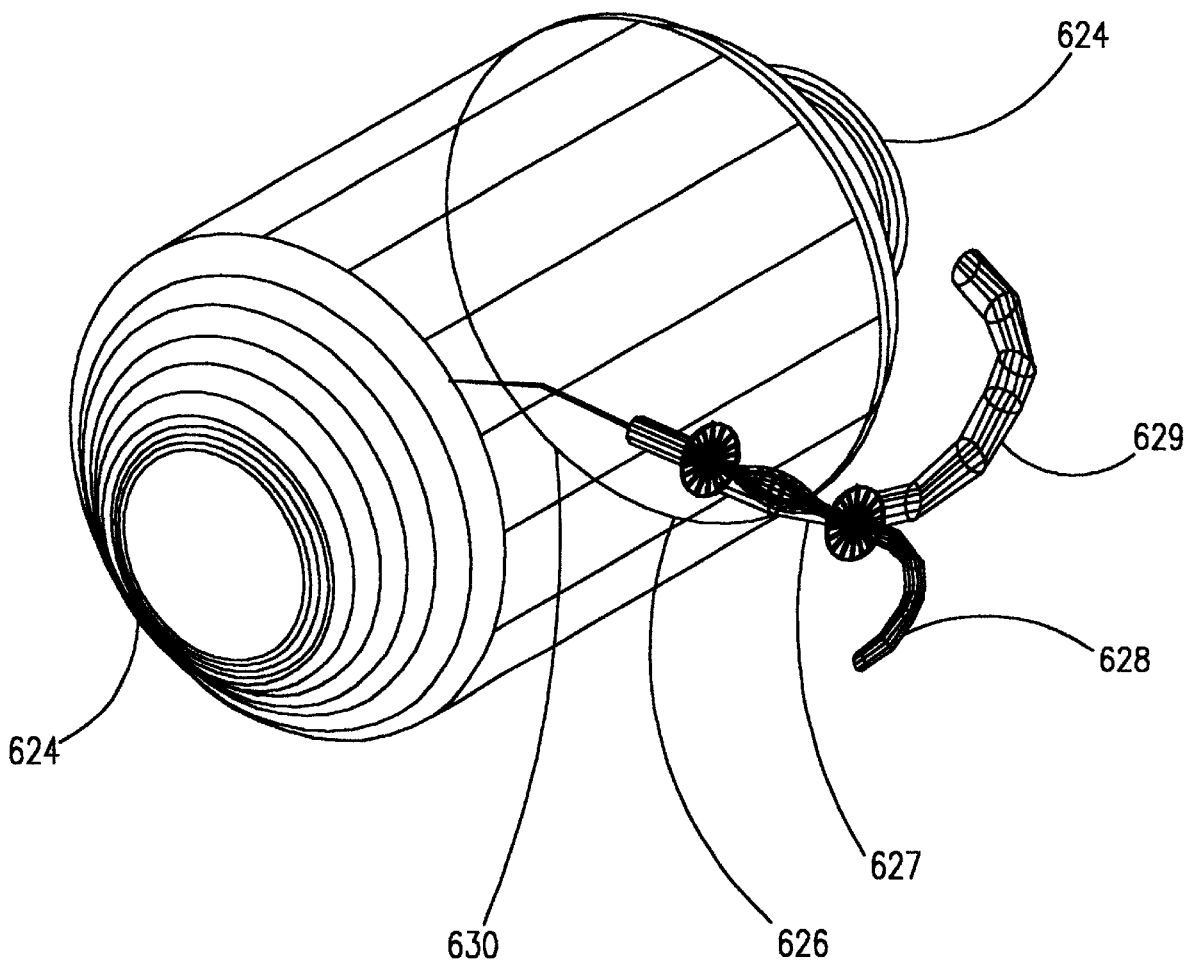
FIG. 6 shows another embodiment of safety means of the present invention.

FIG. 6 illustrates yet another embodiment that overcomes the safety problem of the prior art. A transparent expandable sheet form creates the safety means. When applied, the form is blown up to a balloon through pipe 629. An electrical connection is also included through pipe 629. This serves as the control line for a pressure measurement system. A specific body part is inserted through hole 624. The "balloon" isolates the chosen body part from the surrounding environment. In this embodiment, the pressure inside the balloon is then increased to a specific level. The pressure inside the balloon acts as a gate switch for the laser. If the pressure is sufficiently high, then the treatment site is sufficiently isolated and the laser operation can be started. If the pressure is not high enough, the laser safety switch will not allow the laser to function. Furthermore a safety mechanism is included to prevent over-pressurization and damage to the body part. For the laser safety switch to function, the laser source must also be connected to a central control unit (not shown) either by cable 628 or a wireless transmission method (not shown). The power source for the laser apparatus is included in the form of a battery. Alternatively it is positioned in a central control system and connected via a line in pipe 628. The laser apparatus, itself, is formed by hand-piece 627 and application end 626. The interior balloon surface is coated to ensure isolation from radiation. The application section of the apparatus is inside the balloon while the hand-piece remains outside. This enables the operator to position the device safely.

In another embodiment a pair of gloves is included (not shown). In this latter embodiment, the whole laser hand-piece is inside the balloon. The operator uses the gloves to work completely inside the balloon. This is an advantage for treatments requiring multi-spot treatment irradiation, where small areas distributed over a larger area of the body need treatment. Balloon foil (630) is coated in a dichroitic way. This coating completely reflects radiation generated by the laser source, but is still transparent to other wavelengths. The system in FIG. 6 is in particular constructed to irradiate human extremities. In an alternative, minor modifications are made to this design for the irradiation of a torso. In this alternative the dimensions and hole 624 sizes must be altered appropriately. To apply the radiation, a needle system is shown in FIG. 6, similar to that used in interstitial laser therapy. The needle system is guided into a lumen and used to irradiate specific parts of body.

Figure 7:
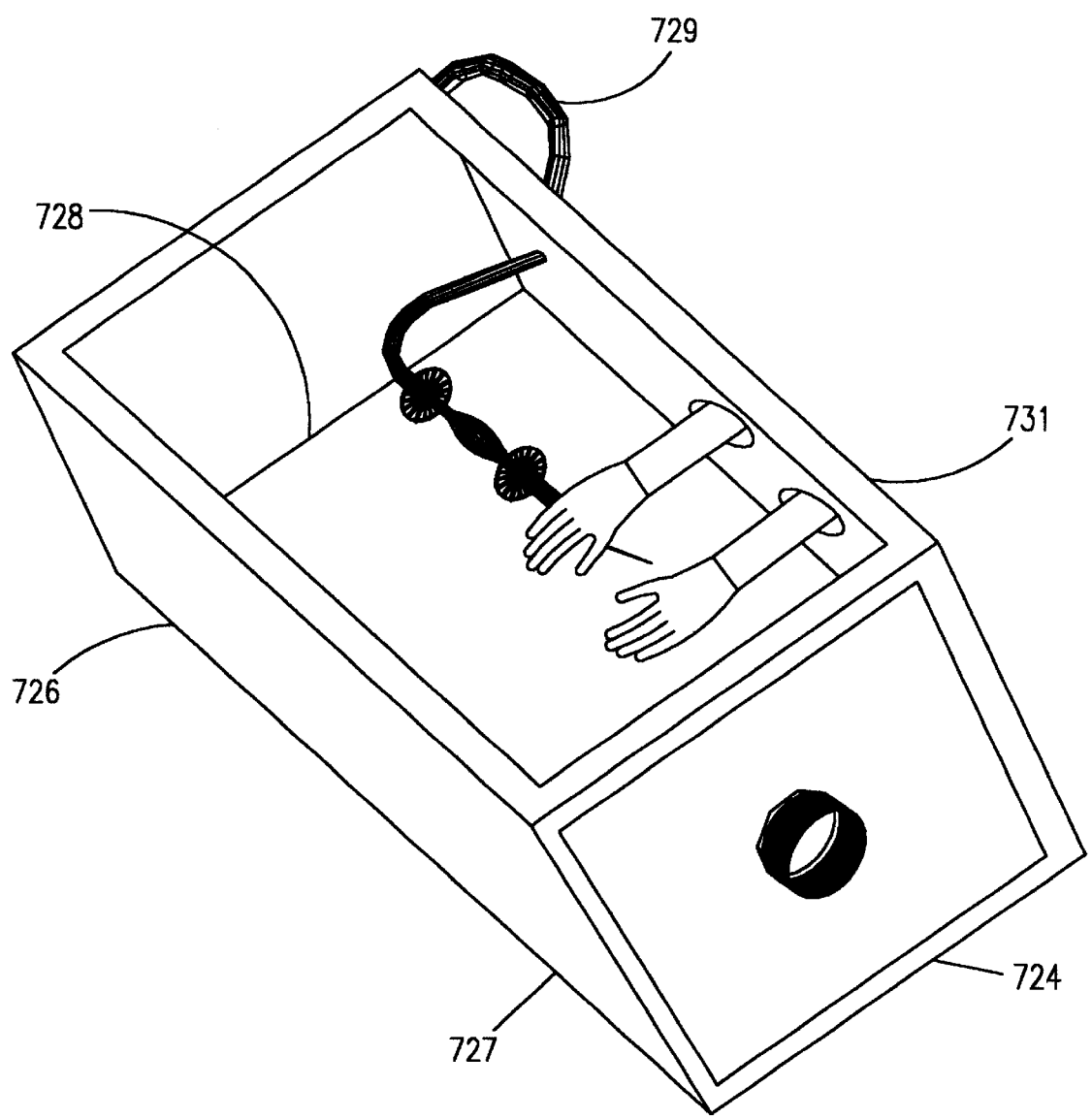
FIG. 7 depicts yet another embodiment of a closed box safety measure of the present invention.

FIG. 7 shows another solution to the general problem of combining laser safety with in situ inspection and ease of use. This embodiment consists of the setup illustrated in FIG. 5 of a closed box (523). One side however is replaced with dichroicly coated window 725 for an observation interface that prevents laser radiation from leaving the enclosed treatment area and entering the environment. At least one central line enters the chamber. Included in the central line are the supply lines for the laser system such as optical fibers, wire lines, vacuum lines and fluid lines as well as a pressure or vacuum safety system. The part of the body to be treated is inserted into the chamber through hole 724. In the embodiment depicted in FIG. 7, hole 724 is specially designed for legs or arms. The whole setup can be scaled to include the patient's entire body. After the body part is inserted, the interface is then sealed and the chamber is evacuated or filled with air or gas to a predetermined pressure. This critical pressure, whether over pressurized or a vacuum, is the triggering criterion for the laser safety mechanism. If the predetermined pressure is not reached, the beam source cannot be started. This assures that the isolation process is complete and no radiation can exit the chamber. In a preferred embodiment, the laser source rests completely inside the chamber. The interface to the outside is realized through preferably a pair of gloves (731), which allow the operator to manipulate the instrument inside the chamber. These gloves are made of a durable material, which has a special coating to protect the practitioners' hands and arms from the irradiation. The advantage of this embodiment over the simple handle interface in FIG. 5 is that more complex operations can be performed. It is possible to perform several steps in a single treatment session without the need to depressurize/deflate the chamber and change setups.

In alternative embodiments to all the described alternatives, a plurality of additional elements can be lead into the treatment zone through the available interface. For some purposes, e.g. interstitial methods, it is particularly useful to include an endoscopic line through the interface that allows for visualization. This is necessary for in-body treatments, where visualization of the treatment area is not possible. In an alternative embodiment means are included that allow the basic parameters of the beam source to be adjusted.

In alternative embodiments a plurality of power source options can be utilized. In one embodiment the power source is at least one rechargeable battery. Alternatively the present invention includes a plug interface to allow batteries to be exchanged without interrupting the power flow. In yet another alternative the present invention includes a power adapter, which allows a direct plug connection.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A laser safe treatment system, wherein a treatment site can be visually inspected safely concurrent with laser treatment, without the need for protective eyewear, comprising:

at least one power source;

at least one laser source and lightguiding means to transmit a beam from said at least one laser source to said treatment site, said at least one power source to activate said at least one laser source;

means to effectively enclose said treatment site;

means to visually inspect said treatment site safely such that a main laser wavelength is filtered to safe levels;

wherein said means to enclose said treatment site is an enclosure, having a soft deformable cushion attached to an edge of said enclosure, that is in contact with said treatment site, to create a better seal between said enclosure and said treatment site.

2. A laser safe treatment system according to claim 1 wherein said enclosure is a semitransparent applicator bell which blocks said main laser wavelength.

3. A laser safe treatment system according to claim 2 wherein said applicator bell is manufactured from a material chosen from the group: dichroicly coated material, colored material, which absorbs strongly said main laser wavelength, and main wavelength absorbing polymeric material.

4. A laser safe treatment system according to 2 further comprising a safety power control mechanism that will only allow said laser source to operate when a seal has been created between said bell and said treatment site.

5. A laser safe treatment system according to claim 2, wherein said bell is manufactured from a flexible material to create a better seal between said bell and said treatment site.

6. A laser safe treatment system according to claim 2 wherein said bell's shape is chosen from group: conical, spherical, or parabolic.

7. A laser safe treatment system according to claim 2 further comprising means for in situ addition of a therapeutic substance through a lumen/catheter passing through said bell.

8. A laser safe treatment system according to claim 1, wherein said attachment of said cushion is a temporary adhesive on said cushion's surface which allows said cushion to be replaced/interchanged.

9. A laser safe treatment system according to claim 1, further comprising:
   at least one vacuum line;
   a minimum of one pressure measurement system connected to said enclosure;
   means to enclose a specific area of said treatment site; and
   a control system, which only allows operation when a predetermined reduced pressure is reached inside said means to enclose said specific area.

10. A laser safe treatment system according to claim 1, wherein said enclosure is a closed box with at least one laser safe inspection window.

11. A laser safe treatment system according to claim 10, wherein said window in said closed box is manufactured from a material chosen from the group: dichroicly coated material, colored material, which absorbs strongly said main laser wavelength, and main wavelength absorbing polymeric material.

12. A laser safe treatment system according to claim 10, further comprising at least one vacuum or pressure line, and a pressure based safety system wherein said laser operation is only possible when a critical pressure level is reached inside the chamber.

13. A laser safe treatment system according to claim 10, further comprising an electrical control mechanism that detects and assures that an interface between said closed box and said treatment site is sealed.

14. A laser safe treatment system according to claim 10, wherein said closed box is further comprised of an interface between the outside environment and said treatment area and wherein said interface is at least one specially coated glove to allow manipulation of the treatment area.

15. A laser safe treatment system according to claim 1, wherein said enclosure is a transparent expandable sheet form and further comprising means to inflate said expandable form.

16. A laser safe treatment system according to claim 15, wherein said transparent form is manufactured from a material chosen from the group: dichroicly coated material, colored material, and main wavelength absorbing plastic polymer.

17. A laser safe treatment system according to claim 1, further comprising a pressure measurement system which serves as a gate switch for said laser safe treatment system wherein said laser safe treatment system will not operate until a specific pressure has been reached within said enclosure.

18. A laser safe treatment system according to claim 1, further comprising means to provide full rotational control of an irradiation spot generated by said laser source and transmitted by said lightguiding means into said enclosure.

19. A laser safe treatment system according to claim 1, further comprising means to adjust basic parameters of said laser source.

* * * * *